United States Patent

Pientka et al.

[11] Patent Number: 6,064,059
[45] Date of Patent: May 16, 2000

[54] DEVICE FOR DETECTING THE LEVEL OF HUMIDITY ON A PANE

[75] Inventors: Rainer Pientka, Achern; Manfred Throl, Wetzlar, both of Germany

[73] Assignee: Robert Bosch GmbH, Stuttgart, Germany

[21] Appl. No.: 08/945,823

[22] PCT Filed: Feb. 26, 1997

[86] PCT No.: PCT/DE97/00335

§ 371 Date: Nov. 5, 1997

§ 102(e) Date: Nov. 5, 1997

[87] PCT Pub. No.: WO97/32762

PCT Pub. Date: Sep. 12, 1997

[30] Foreign Application Priority Data

Mar. 6, 1996 [DE] Germany .......................... 196 08 648

[51] Int. Cl.[7] .................................................. G01N 21/17
[52] U.S. Cl. ............................. 250/227.24; 250/227.25; 250/577; 340/602; 318/483; 318/DIG. 2
[58] Field of Search ........................ 250/227.24, 227.25, 250/573, 574, 577; 73/29.01; 318/483, DIG. 2; 340/602; 356/136, 445

[56] References Cited

U.S. PATENT DOCUMENTS 4,676,638  6/1987  Yasuda ..................................... 250/573
5,661,303  8/1997  Teder ................................... 250/227.25

FOREIGN PATENT DOCUMENTS 3806881   9/1989   Germany .
4202121  12/1992   Germany .
4329609   2/1995   Germany .
4406398   8/1995   Germany .

*Primary Examiner*—Stephone B. Allen
*Attorney, Agent, or Firm*—Venable; George Spencer; Norman Kunitz

[57] ABSTRACT

An arrangement for detecting moisture conditions on a pane, particularly a windshield of a motor vehicle, wherein radiation emitted by a transmitter is coupled by a radiation guide into the pane and is coupled out of the pane onto a receiver. With respect to the production and the dimensions, the design is supported by the measures which provide that the beam entry surface and/or the beam exit surface is/are arranged on the parallel side of the radiation guide facing the circuit board, and that the optical axis of the transmitter or of the receiver is oriented to be perpendicular to the beam entry surface or the beam exit surface and that the radiation guide has at least one input-end or output-end deviating surface with which the radiation that entered the radiation guide is guided at a right angle into the interior of the radiation guide or the radiation which is to be oriented out of the radiation guide onto the receiver is guided at a right angle out of the interior of the radiation guide.

13 Claims, 1 Drawing Sheet

DEVICE FOR DETECTING THE LEVEL OF HUMIDITY ON A PANE

STATE OF THE TECHNOLOGY

The invention relates to an arrangement for detecting moisture conditions on a pane, particularly a windshield of a motor vehicle, the arrangement having a radiation transmitting device which is supported on a circuit board and has at least one transmitter, having a beam guide which can be coupled to the pane and is oriented essentially parallel to the circuit board and is provided with a beam entry surface to receive the emitted radiation and with a beam exit surface to emit the radiation, and having a radiation receiving device which receives the exiting radiation and is also supported on the circuit board and which has at least one receiver.

An arrangement of this type is specified as being known in DE 44 06 398 A1. In this known arrangement in the form of a rain sensor, which can be attached on the windshield of a motor vehicle, a circuit board is arranged parallel to a flat longitudinal plane of a transparent light guide by means of which light is coupled into and out of the pane; the circuit board is connected to a second board by means of elastic connecting lines. Seated in holders, a transmitter and a receiver are connected on the circuit board, which transmitter and receiver project with their light-emitting or light-receiving element approximately into a center plane of the light guide, which is disposed parallel to the plane of the circuit board, in such a way that the optical axes of the transmitter and of the receiver are also substantially disposed in the center plane of the light guide so as to couple the light into and out of the light guide. The arrangement of this type of the transmitter and receiver requires a relatively large structural space and additional assembly steps during production, during which process attention must be paid to a precise positioning of the transmitter and of the receiver with respect to the light guide or radiation guide.

SUMMARY AND ADVANTAGES OF THE INVENTION

It is the object of the invention to make available an arrangement of the type specified at the outset which is simpler to produce and results in a design which saves more space.

This object is accomplished according to the invention by an arranged for detection moisture conditions on a pane, particulary the windshield of a motor vehicle; of the type described above wherein the beam entry surface and/or the beam exit surface is/are arranged on the parallel side of the radiation guide facing the circuit board, and that the optical axis of the transmitter or of the receiver is oriented to be perpendicular to the beam entry surface or the beam exit surface and that the radiation guide has at least one input-end or output-end deflecting surface with which the radiation that entered the radiation guide is guided at a right angle into the interior of the radiation guide or the radiation which is to be oriented out of the radiation guide onto the receiver is guided at a right angle out of the interior of the radiation guide. On the basis of these measures, transmitters and/or receivers can be arranged on the board without complex holders, thus also ensuring a precise positioning in a simple manner. The radiation guide can be produced as simply as was possible so far by means of corresponding shaping. Apart from the simpler production, the design also saves space and results in a miniaturization of the entire arrangement; it is possible in conjunction with other measures to use only one circuit board.

If it is provided that the at least one transmitter and the at least one receiver are configured as SMD (surface mounted device) components, the transmitter and the receiver can be mounted on the circuit board during the same operational step with which the remaining electrical components are mounted, thus further simplifying the production. This also accomplishes a very precise positioning of the transmitter and of the receiver.

The measure which provides that the beam entry surface and/or the beam exit surface are configured as convergent lenses permits the positioning of the transmitter and of the receiver at a short distance from the beam entry surface or the beam exit surface, with the beam bundle emitted by the transmitter and the beam bundle irradiated into the receiver practically being captured completely. The distance between transmitter and beam entry surface or receiver and beam exit surface can be further reduced by the measure which provides that the convergent lenses of the beam entry surface and of the beam exit surface are configured as Fresnel lenses or as several individual lens elements arranged on a flat surface or that the beam entry surface and the beam exit surface are provided with these two types of convergent lenses in a manner which differs alternatingly. Here, for example, the beam entry surface can be provided with individual lens elements and the beam exit surface with a Fresnel lens or vice versa if the transmitter elements or receiver elements are very small. In this context, the individual lens elements permit the arrangement of a corresponding number of associated transmitter elements or receiver elements on the circuit board so that the total radiation power of the emitted or received radiation can be increased accordingly.

A simple configuration of the radiation guide is accomplished in that the deflecting surfaces are provided on the side of the radiation guide facing away from the circuit board and are inclined at an angle of 45° with respect to the plane of the circuit board when seen in a plan view of the long narrow side of the circuit board.

A further option for the beam guidance and the optimum matching of the radiation bundles to the geometries of transmitter, light guide and receiver is made possible in that the radiation guide is provided with several deviating surfaces with which the emitted radiation in an input-end section is guided into the pane and the radiation coming from the pane in an output-end section is guided onto the output-end deflecting surface and that at least one of the deviating surfaces and/or a deflecting surface is curved convexly outward or concavely inward to converge or to diverge the radiation, with a reflection through total reflection being maintained. In this process, a concentration or expansion of the radiation can be accomplished in that the curvature is configured to be toroidal.

An advantageous design with components that are available at present is comprised in that, e. g., several transmitters are provided with which respectively a separate lens element is associated on the beam entry surface and that a receiver is provided with which a Fresnel lens is associated on the beam exit surface.

A simplification of the optical design is accomplished in that the convergent lenses are configured to be spherical.

The invention is explained below in greater detail by way of an embodiment with reference to the figures.

DETAILED DESCRIPTION OF THE PREFERRED EMBODIMENTS

Figure 1:
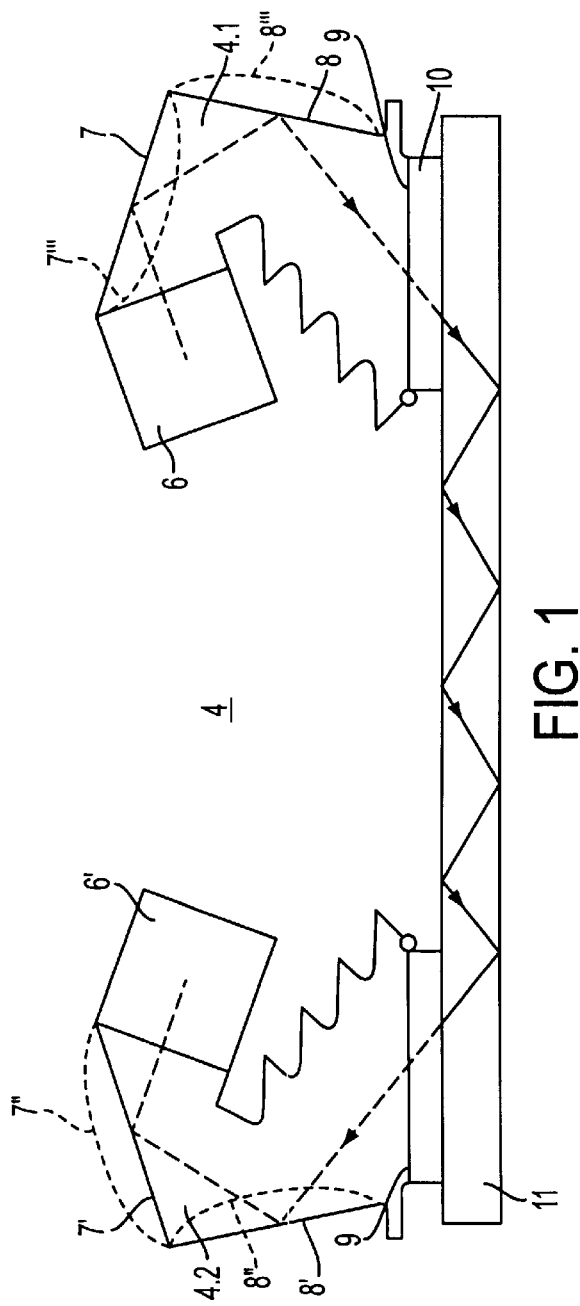
FIG. 1 is a front view of the arrangement for detecting moisture conditions on a pane in a state in which the arrangement is coupled to the pane.

The arrangement shown in FIG. 1 has a radiation guide 4 having an input-end section 4.1 and an output-end section 4.2 relative to the beam path. The input-end section 4.1 and the output-end section 4.2 are each coupled to the pane via a silicone cushion 10 opposite the outer side of the pane 11 so that the beam path (identified through arrows) extends through the interior of the pane 11 in the region between the input-end section 4.1 and the output-end section 4.2 which is at a distance from the input-end section through the interior of pane 11. Adjacent to the silicone cushions 10, the input-end section 4.1 and the output-end section 4.2 are provided with suitable coupling surfaces 9. For beam guidance, radiation guide 4 is further provided with first deviating surfaces 7, 8 and second deviating surfaces 8', 7' with which the beam is deviated in the drawing plane according to FIG. 1.

Figure 2:
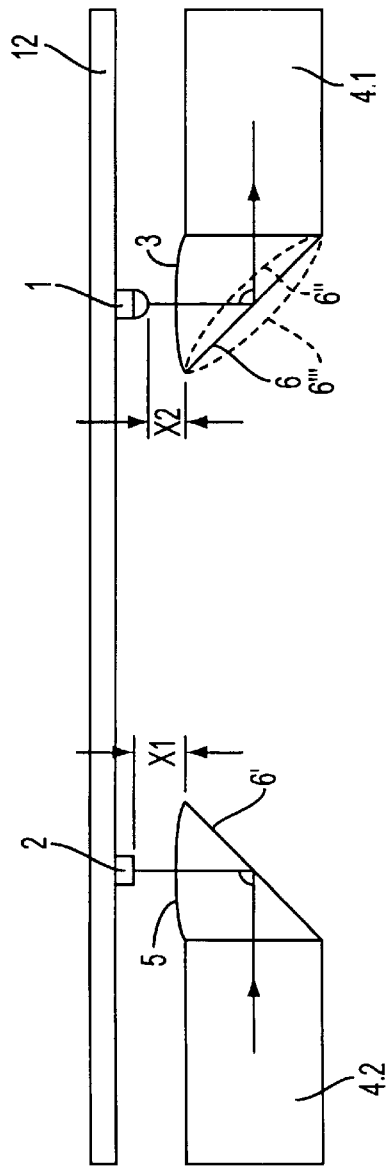
FIG. 2 is the arrangement according to FIG. 1 in plan view.

Furthermore, the input-end section 4.1 and the output-end section 4.2 of the radiation guide 4 have deflecting surfaces 6 or 6', respectively, in the region of their input or output which guide a beam impinging perpendicularly to the drawing plane or being guided out perpendicularly to the drawing plane into or out of the radiation guide 4. The orientation of the input-end deflecting surface 6 and of the output-end deflecting surface 6' is illustrated in FIG. 2 which represents a plan view. According to FIG. 2, a circuit board 12 is arranged parallel to the rear plane of the radiation guide 4, on which circuit board a transmitter 1 and a receiver 2, available in SMD technology, are mounted. Opposite the transmitter, at a relatively small distance x2, there is arranged a beam entry surface 3 of the input-end section 4.1, while opposite the receiver 2, also at a relatively small distance x1, a beam exit surface of the output-end section 4.2 is arranged. The beam emitted by the transmitter 1 is guided at a right angle into the radiation guide 4 at the input-end deflecting surface 6 oriented at a 45° angle with respect to the plane of the circuit board 12 so that it is guided, as illustrated in FIG. 1, through the radiation guide parallel to the plane of the circuit board 12 up to the output-end deflecting surface 6' which is also oriented at a 45° angle with respect to the plane of the circuit board 12. The beam, which is deflected at a right angle on the output-end deflecting surface 6' reaches the correspondingly positioned receiver 2 via the beam exit surface 5. Just like the circuit board 12, the deflecting surfaces 6, 6' shown in FIG. 2 are oriented perpendicularly relative to the drawing plane.

Figure 3:
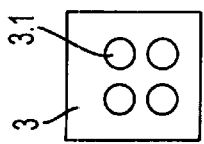
FIG. 3 is a beam entry surface or beam exit surface with several individual lens elements.

In order to completely capture and optimally exploit the radiation bundle emitted by the transmitter 1 and to guide it into the radiation guide, the beam entry surface 3 is configured as a convergent lens which is curved outwardly, and the beam exit surface 5 is also configured as a convergent lens that is curved outwardly so as to guide the radiation leaving the radiation guide 4 entirely onto the receiver 2. Frequently, the transmitters 1 configured in SMD technology are relatively small so that it is advantageous to mount several, e. g., four, transmitter elements to increase the radiation power coupled into the radiation guide 4. The beam entry surface 3 can then have lens elements 3.1 associated with the individual transmitter elements, as illustrated in FIG. 3, which lens elements are configured and arranged in size, curvature and distance from the transmitter 1 to correspond to the emitted beam bundle. Correspondingly, several receiving elements can also be provided and the output-end deflecting surface 6' can be provided with corresponding lens elements like the input-end deflecting surface 6. But usually, the receivers in the form of photodiodes available in SMD technology are larger in their dimensions than the transmitters 1 configured as transmitter diodes. For the design of the beam exit surface 5, it is advantageous in this case and in other cases for the convergent lens to be embodied as a Fresnel lens so that, overall, a relatively flat structure is accomplished in spite of a relatively large curvature and collimation characteristic or concentration characteristic. If necessary, the beam entry surface 3 can also be configured as a Fresnel lens structure. All convergent lenses can be shaped spherically to simplify the production because precise imaging properties are less important than an even, controllable light guidance.

In order to expand or to converge the radiation bundle guided through the radiation guide 4, the input-end and output-end deflecting surface 6, 6' as well as the first and second deviating surfaces 7, 8, 7' and 8' can also be curved in a convex 6, 7, 8 or concave 6, 7, 8 manner, e. g., toroidally. It is also possible for only some of these surfaces to have a corresponding curvature for the beam shaping. For example, in the input-end section 4.1 of the radiation guide an expansion can be accomplished by means of negative toroidal surfaces, i. e., of surfaces curved inwardly, and in the output-end section 4.2 of the radiation guide 4 a convergence of the beam bundle by means of positive surfaces, i. e., of surfaces curved outwardly, so as to achieve an optimum utilization of the radiation guide and a concentration on the receiver 2.

The configuration and arrangement of the transmitter 1 and of the receiver 2 in SMD technology allow a simple mounting of components on the circuit board in the same operational step in which the other components are applied as well. In this process, the positioning and orientation of the transmitter 1 and of the receiver 2 are always very precise so that no additional measures are necessary in this regard. The arrangement and the relatively small dimensions of the transmitter 1 and of the receiver 2 also result in more space on the circuit board 12 and a more favorable positioning option for other electrical components which serve to process signals. It has turned out that the measures described permit the use of only one circuit board which in its dimensions approximately corresponds to the outside dimensions of the radiation guide.

We claim:

1. An arrangement for detecting moisture conditions on a pane, with the arrangement having a radiation transmitting device which is supported on a circuit board and has at least one transmitter; a radiation guide which can be coupled to the pane and is oriented essentially parallel to the circuit board, which is provided with a beam entry surface to receive the emitted radiation; and a radiation receiving device which receives the exiting radiation and is also supported on the circuit board and which has at least one receiver; and wherein:

the beam entry surface (3) and the beam exit surface (5) 14 are arranged on a respective parallel side of the guide (4) facing the circuit board (12); the optical axis of the transmitter (1) or of the receiver (2) is oriented to be perpendicular to the beam entry surface (3) or the beam exit surface, respectively; (5) the radiation guide (4) has at least one input-end or output-end deflecting surface (6, 6') with which the radiation that entered the radiation guide (4) is guided at a right angle into the interior of the radiation guide (4) or the radiation which is to be oriented out of the radiation guide (4) onto the receiver (2) is guided at a right angle out of the interior of the radiation guide (4) the radiation guide (4) is further provided with several deviating surfaces (7, 8, 7', 8') with which the emitted radiation in an input-end section (4.1) is guided into the pane (11) and the radiation coming from the pane (11) in an output-end section (4.2) is guided into the output-end deflecting surface (6'); and at least one of the deviating surfaces (7, 8, 7', 8') and at least one of the deflecting surfaces (6, 6') is curved convexly outward or concavely inward to respectively converge or diverge the radiation, with a reflection through total reflection being maintained.

2. An arrangement according to claim 1, wherein the at least one transmitter (1) and the at least one receiver (2) are Surface Mounted Device (SMD) components.

3. An arrangement according to claim 1, wherein the deflecting surfaces (6, 6') are provided on the side of the radiation guide (4) facing away from the circuit board (12) and are inclined at an angle of 45° with respect to the plane of the circuit board (12) when seen in a plan view of the long narrow side of the circuit board (12).

4. An arrangement according to claim 1, wherein the curvature is toroidal.

5. An arrangement according to claim 1 wherein the pane is a windshield of a motor vehicle.

6. An arrangement according to claim 1 wherein, the beam entry surface (3) and the beam exit surface (5) are configured as convergent lenses.

7. An arrangement according to claim 6, wherein the convergent lenses are configured to be spherical.

8. An arrangement according to claim 6, wherein the convergent lenses of the beam entry surface (3) and of the beam exit surface (5) are configured as Fresnel lenses, or as several individual lens elements (3.1) arranged on a flat surface, or the beam entry surface (3) and the beam exit surface (5) are provided with these two types of convergent lenses in a manner which differs alternatingly.

9. An arrangement according to claim 8, wherein several transmitters (1) are provided with which respectively a separate lens element (3.1) is associated on the beam entry surface (3), and that a receiver (2) is provided with which a Fresnel lens is associated on the beam exit surface (5).

10. An arrangement for detecting moisture conditions on a pane, with the arrangement having: a radiation transmitting device which is supported on a circuit board and has at least one transmitter; a radiation guide which can be coupled to the pane and is oriented essentially parallel to the circuit board, is provided with a beam entry surface to receive the emitted radiation; and a radiation receiving device which receives the exiting radiation and is also supported on the circuit board and which has at least one receiver; and wherein:

the beam entry surface (3) and the beam exit surface (5) are arranged on a respective parallel side of the radiation guide (4) facing the circuit board (12); the optical axis of the transmitter (1) or of the receiver (2) is oriented to be perpendicular to the beam entry surface (3) or the beam exit surface (5), respectively; the radiation guide (4) has at least one input-end or output-end deflecting surface (6, 6') with which the radiation that entered the radiation guide (4) is guided at a right angle into the interior of the radiation guide (4) or the radiation which is to be oriented out of the radiation guide (4) onto the receiver (2) is guided at a right angle out of the interior of the radiation guide (4); the beam entry surface (3) and the beam exit surface (5) are configured as convergent lenses; and, the convergent lenses of the beam entry surface (3) and of the beam exit surface (5) are configured as Fresnel lenses, as several individual lens elements (3.1) arranged on a flat surface, or as alternating ones of these two types of convergent lenses on the beam entry surface (3) and the beam exit surface (5).

11. An arrangement according to claim 10 wherein several transmitters (1) are provided with which a respective separate lens element (3.1) is associated on the beam entry surface (3), and a receiver (2) is provided with which a Fresnel lens is associated on the beam exit surface (5).

12. An arrangement according to claim 10 wherein the convergent lenses are configured to be spherical.

13. An arrangement for detecting moisture conditions on a windshield of a motor vehicle, with the arrangement having at least one transmitter (1), a beam guide (4) that can be coupled to the pane (11), and at least one receiver (2); and wherein the optical axes of the transmitter (1) and the receiver (2) are oriented perpendicular to a beam entry surface (3) and a beam exit surface (5), respectively of the beam guide (4); the beam guide (4) has at least one deflection surface (6, 6') on the incoming side and on the outgoing side, with which, respectively, the radiation entering the beam guide (4) is deflected totally and at a right angle into the inside of beam guide (4) or with which the radiation coming from the inside of beam guide (4) is deflected totally and at a right angle onto the receiver (2); the beam guide (4) has several deviating surfaces (7, 8, 7', 8'); at least one of the deviating surfaces (7, 8, 7" 8") and at least one of the deflection surfaces (6, 6', 6") is curved convexly toward the outside (7", 8") or concavely toward the inside (7''', 8") to converge or diverge the beam, wherein a mirror reflection is maintained through total reflection.

* * * * *